(12) United States Patent
O'Day

(10) Patent No.: US 10,569,037 B2
(45) Date of Patent: Feb. 25, 2020

(54) NASOPHARYNGEAL DEVICE FOR OBSTRUCTIVE SLEEP APNEA SYNDROME

(71) Applicant: John M. O'Day, Somersworth, NH (US)

(72) Inventor: John M. O'Day, Somersworth, NH (US)

( * ) Notice: Subject to any disclaimer, the term of this patent is extended or adjusted under 35 U.S.C. 154(b) by 230 days.

(21) Appl. No.: 14/621,722

(22) Filed: Feb. 13, 2015

(65) Prior Publication Data
US 2015/0230969 A1  Aug. 20, 2015

Related U.S. Application Data

(60) Provisional application No. 61/939,759, filed on Feb. 14, 2014.

(51) Int. Cl.
*A61F 5/00* (2006.01)
*A61M 16/04* (2006.01)
*A61F 5/56* (2006.01)

(52) U.S. Cl.
CPC ........... *A61M 16/0429* (2014.02); *A61F 5/56* (2013.01); *A61M 16/0434* (2013.01); *A61M 16/0461* (2013.01); *A61M 16/0488* (2013.01)

(58) Field of Classification Search
CPC ....... A61F 5/56; A61J 15/0003; A61M 29/00; A61M 16/0666; A61M 16/0434; A61M 16/0461; A61M 16/0429; A61M 16/0488; A61M 3/0295; A61M 2025/0226; A61B 17/12
USPC ................. 128/848, 204.12, 207.18; 604/79; 600/115–116
See application file for complete search history.

(56) References Cited

U.S. PATENT DOCUMENTS

| | | | | |
|---|---|---|---|---|
| 3,049,125 A | * | 8/1962 | Kriwkowitsch | A61B 17/12104 604/100.02 |
| 3,568,678 A | * | 3/1971 | Pourquier | A61M 16/0666 128/207.18 |
| 3,903,893 A | * | 9/1975 | Scheer | A61B 17/12045 604/101.05 |
| 3,915,173 A | * | 10/1975 | Brekke | A61B 17/12022 128/207.15 |
| 4,464,175 A | * | 8/1984 | Altman | A61M 3/0295 600/116 |
| 4,821,715 A | | 4/1989 | Downing | |

(Continued)

OTHER PUBLICATIONS

International Search Report for International Application No. PCT/US2016/054123 dated Dec. 19, 2016, 4 pages.

(Continued)

*Primary Examiner* — Keri J Nelson
*Assistant Examiner* — Adam Baker
(74) *Attorney, Agent, or Firm* — TraskBritt

(57) ABSTRACT

The system and method for reducing or eliminating obstructive sleep apnea in patients with the use of a nasopharyngeal device. The nasopharyngeal device has at least one cup and a balloon-cuff located at opposing ends of a semi-rigid, solid-walled tube. The balloon-cuff is reversibly inflatable and is located adjacent to the soft palate of a patient when installed. The inflation of the balloon-cuff opens the airway in a patient thereby reducing obstructive sleep apnea. The one or more cups have perforations, holes, slots or the like for increasing air intake. The cups may also contain clips for securing the nasopharyngeal device in place.

20 Claims, 14 Drawing Sheets

(56) References Cited

U.S. PATENT DOCUMENTS

| | | | |
|---|---|---|---|
| 5,105,807 A * | 4/1992 | Kahn | A61M 25/02 |
| | | | 128/200.26 |
| 5,752,511 A * | 5/1998 | Simmons | A61F 5/08 |
| | | | 128/206.11 |
| 6,183,493 B1 | 2/2001 | Zammit | |
| 6,394,093 B1 * | 5/2002 | Lethi | A61M 16/0461 |
| | | | 128/207.13 |
| 6,536,437 B1 * | 3/2003 | Dragisic | A61M 16/04 |
| | | | 128/207.14 |
| 7,100,612 B2 | 9/2006 | Dunlap | |
| 8,428,727 B2 | 4/2013 | Bolea et al. | |
| 8,833,373 B2 | 9/2014 | Barodka | |
| 2005/0240147 A1 | 10/2005 | Makower et al. | |
| 2006/0085027 A1 * | 4/2006 | Santin | A61F 5/08 |
| | | | 606/199 |
| 2006/0283464 A1 | 12/2006 | Dunlap | |
| 2008/0053458 A1 | 3/2008 | De et al. | |
| 2009/0044814 A1 | 2/2009 | Iancea et al. | |
| 2009/0064999 A1 | 3/2009 | Marten et al. | |
| 2009/0266365 A1 | 10/2009 | Oberle | |
| 2010/0217302 A1 | 8/2010 | Oberle | |
| 2010/0242967 A1 | 9/2010 | Burbank et al. | |
| 2010/0319708 A1 | 12/2010 | Mahr et al. | |
| 2011/0100376 A1 | 5/2011 | Rousseau | |
| 2011/0178439 A1 | 7/2011 | Irwin | |
| 2011/0226264 A1 * | 9/2011 | Friedman | A61F 5/566 |
| | | | 128/848 |
| 2011/0240038 A1 | 10/2011 | Doshi et al. | |
| 2012/0118286 A1 | 5/2012 | Barodka | |
| 2012/0118297 A1 | 5/2012 | Barodka | |
| 2013/0152940 A1 | 6/2013 | Larson et al. | |
| 2013/0319427 A1 | 12/2013 | Sung et al. | |

OTHER PUBLICATIONS

Written Opinion of the International Searching Authority for International Application No. PCT/US2016/054123 dated Dec. 19, 2016, 7 pages.

International Preliminary Report on Patentability for International Application No. PCT/US2015/015827 dated Aug. 16, 2016, 7 pages.

International Search Report and Written Opinion dated Jun. 1, 2015 for corresponding International Patent Application PCT/US15/1582, 8 pages.

* cited by examiner

HEAD AND NECK ANATOMY

NASOPHARYNGEAL DEVICE FOR OBSTRUCTIVE SLEEP APNEA SYNDROME

CROSS-REFERENCE TO RELATED APPLICATIONS

The present application claims the benefit of Provisional Patent Application Ser. No. 61/939,759 filed Feb. 14, 2014, which is incorporated herein by reference. This application is also related to U.S. patent application Ser. No. 15/278, 285, filed Sep. 28, 2016, pending, for "Nasopharyngeal Device for Obstructive Sleep Apnea Syndrome."

FIELD OF THE INVENTION

The present invention relates to the amelioration of obstructive sleep apnea syndrome and more particularly to a nasopharyngeal device used to reduce or eliminate obstructive sleep apnea episodes.

BACKGROUND OF THE INVENTION

Obstructive sleep apnea syndrome ("OSA") affects millions of Americans and currently the gold standard of treatment is continuous positive airway pressure ("CPAP"), Unfortunately, although CPAP is almost uniformly effective in terms of facilitating a patient's ability to breathe while they sleep, the obtrusive, claustrophobic nature of the various facial interfaces translates into many patients refusing to use the units at night. Therefore, although CPAP therapy is effective there is a very low long-term compliance seen in patients utilizing this modality of treatment. Consequently, health care professionals have sought alternative treatments for nocturnal airway obstruction such as surgery of the palate and tongue base and mandibular advancement devices. No treatment has been found to be uniformly effective in ameliorating OSA. Because of the dynamics of airway obstruction, predicting success with any one treatment plan has also proven to be difficult.

Obstructive sleep apnea syndrome is characterized by obstruction to an individual's ability to breathe while sleeping and the two areas of obstruction are the soft palate and the base of tongue. One aspect of the present invention is a nasopharyngeal device used to assist patients who suffer from OSA. The design is intended to be a non-intrusive nasal device that enables the patient to maintain patency of the nasopharyngeal airway by stenting open the palate, which in the patient with OSA closes upon laying down to sleep.

SUMMARY OF THE INVENTION

One aspect of the present invention is a nasopharyngeal device, comprising a semi-rigid, solid-walled tube having a proximal end and a distal end; a reversibly inflatable balloon-cuff located at the distal end of the tube wherein when inflated the balloon-cuff maintains patency of the nasopharyngeal airway by stenting open the soft palate and defines an area through which air flow is not allowed except through the tube; at least one cup located at the proximal end of the tube; and an inflation port for inflating and deflating the balloon-cuff via the tube.

One embodiment of the nasopharyngeal device is wherein the tube has a length such that the balloon-cuff is proximal to the soft palate when in use.

One embodiment of the nasopharyngeal device is wherein there is a pair of cups.

One embodiment of the nasopharyngeal device further comprises a clip on the cup to secure the device on the patient's nostril.

One embodiment of the nasopharyngeal device is wherein the cup further comprises perforations that may be of various sizes and shapes.

Another aspect of the present invention is a method of reducing obstructive sleep apnea, comprising: providing a nasopharyngeal device, comprising a semi-rigid, solid-walled tube having a proximal end and a distal end; a reversibly inflatable balloon-cuff located at the distal end of the tube wherein when inflated the balloon-cuff maintains patency of the nasopharyngeal airway by stenting open the soft palate and defines an area through which air flow is not allowed except through the tube; at least one cup located at the proximal end of the tube; and an inflation port for inflating and deflating the balloon-cuff via the tube, inserting the nasopharyngeal device into the nasopharyngeal airway; and inflating the balloon-cuff thereby maintaining the pathway of the airway.

One embodiment of the method of reducing obstructive sleep apnea is wherein the tube has a length such that the balloon-cuff is proximal to the soft palate when in use.

One embodiment of the method of reducing obstructive sleep apnea is wherein there is a pair of cups.

One embodiment of the method of reducing obstructive sleep apnea further comprises a clip on the cup to secure the device on the patient's nostril.

One embodiment of the method of reducing obstructive sleep apnea is wherein the cup further comprises perforations that may be of various sizes and shapes.

These aspects of the invention are not Meant to be exclusive and other features, aspects, and advantages of the present invention will be readily apparent to those of ordinary skill in the art when read in conjunction with the following description, appended claims, and accompanying drawings.

BRIEF DESCRIPTION OF THE DRAWINGS

The foregoing and other objects, features, and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Obstructive sleep apnea syndrome is characterized by obstruction to an individual's ability to breathe while sleeping. The two areas of obstruction are the soft palate and the base of tongue. The nasopharyngeal airway is the most frequently obstructed area Involved in patients with OSA.

One aspect of the present invention is a nasopharyngeal device to assist patients who suffer from OSA. The design is intended to be a non-intrusive nasal device that enables the patient to maintain patency of the nasopharyngeal airway by stenting open the palate, which in the patient with OSA closes upon laying down to sleep. By stenting open the nasopharyngeal airway with an embodiment of the present invention, the patient maintains his or her ability to breathe in a recumbent position.

Currently, the gold standard of treatment for OSA is continuous positive airway pressure ("CPAP"). However, the obtrusive, claustrophobic nature of the various facial interfaces causes many patients to refuse to use CPAP units over the long term. Also, patients with OSA can undergo a uvulopalatopharyngoplasty (UPPP) surgical procedure, which is surgically effective in opening up the nasopharyngeal space, but this method requires patients to experience all of the risks associated with a surgical procedure. In contrast, the device of the present invention is non-invasive and will help a large number of patients to reduce or eliminate OSA without any of the risks associated with surgical procedures.

Figure 1:
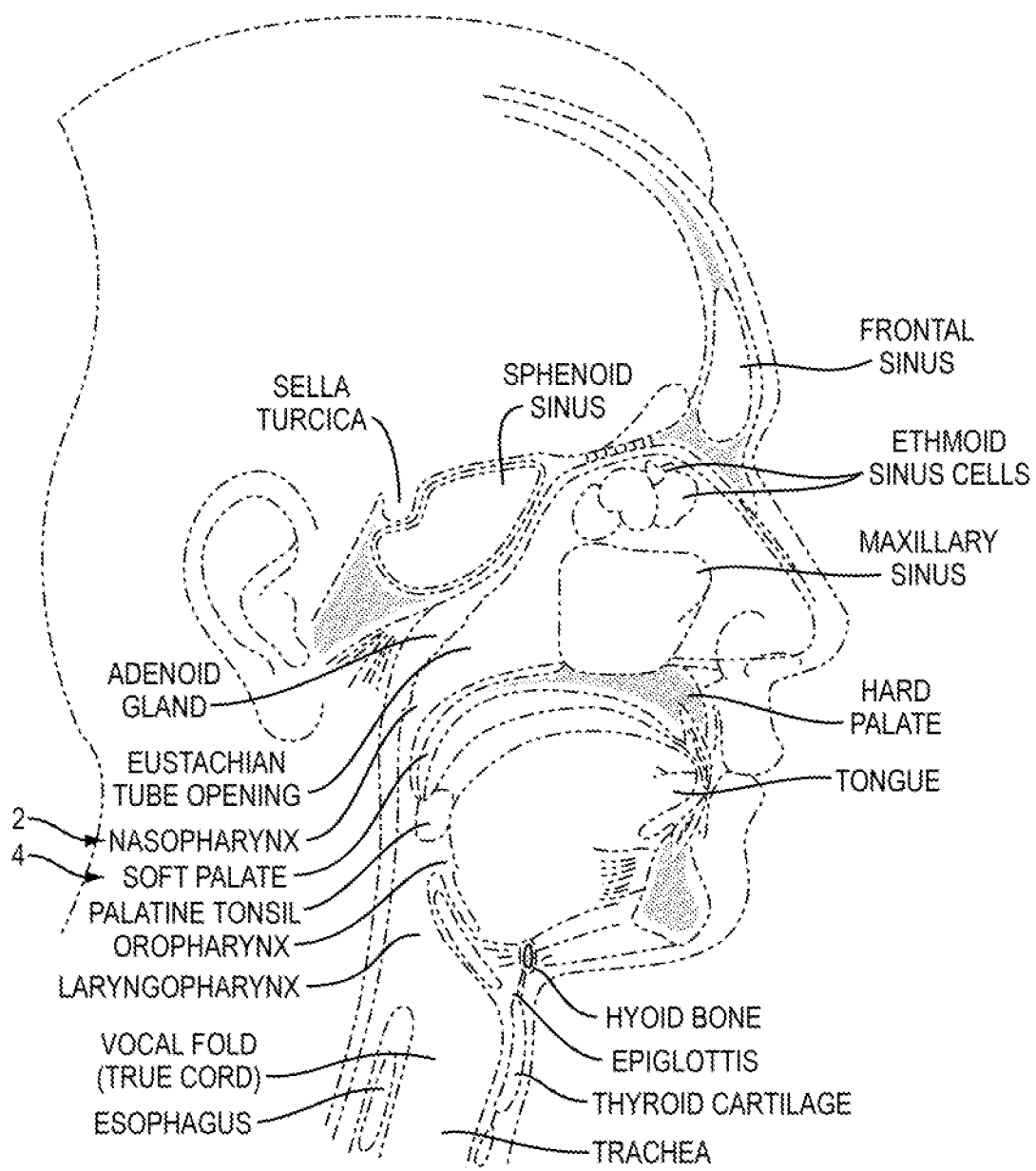
FIG. 1 shows a schematic of the anatomy of a human head and neck.

Referring to FIG. 1, a schematic of the anatomy of a human head and neck is shown. More particularly, the nasopharynx 2 and the soft palate 4 are highlighted and will be referenced later when discussing the insertion and placement of certain embodiments of the present invention.

U.S. Patent Publication No. 2013/0152940 describes a nasopharyngeal trumpet as one possible treatment of OSA. U.S. Patent Publication No. 2006/0283464 describes a nasal trumpet or nasopharyngeal airway as a tube that is designed to be inserted into the nasal passageway to secure an open airway. When a patient becomes unconscious, the muscles in the jaw commonly relax and can allow the tongue to slide back and obstruct the airway. The purpose of the flared end (a.k.a. the trumpet) is to prevent the device from becoming lost inside the patient's nose.

Figure 2A:
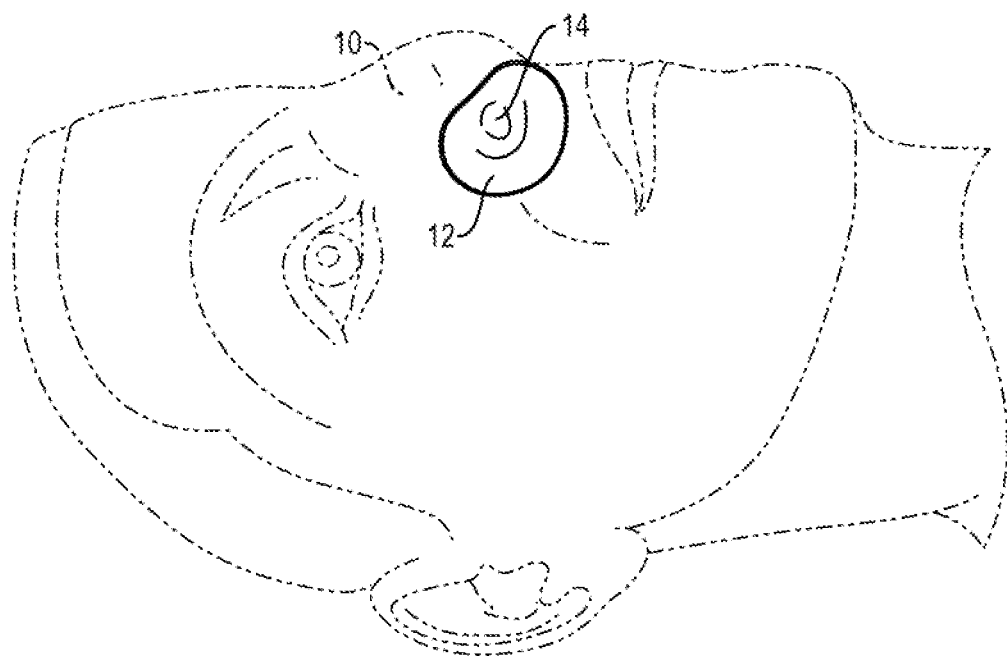
FIG. 2A and FIG. 2B show a prior art nasal trumpet inserted into an anatomical model.

There are several drawbacks to the trumpet design in treating OSA. To begin, the trumpet design obstructs the airway by blocking the nostril with the "trumpet," as seen in FIG. 2A. Still referring to FIG. 2A, a prior art nasal trumpet 10 inserted into the nose of a anatomical model is shown. More particularly, the flange 12 of the trumpet extends beyond the nostril of a patient and blocks air from entering. The patient's air supply is directed through the opening of the tube 14 in the trumpet 10 and the volume of air available to the patient per breath is limited by the diameter of the tube.

Figure 2B:
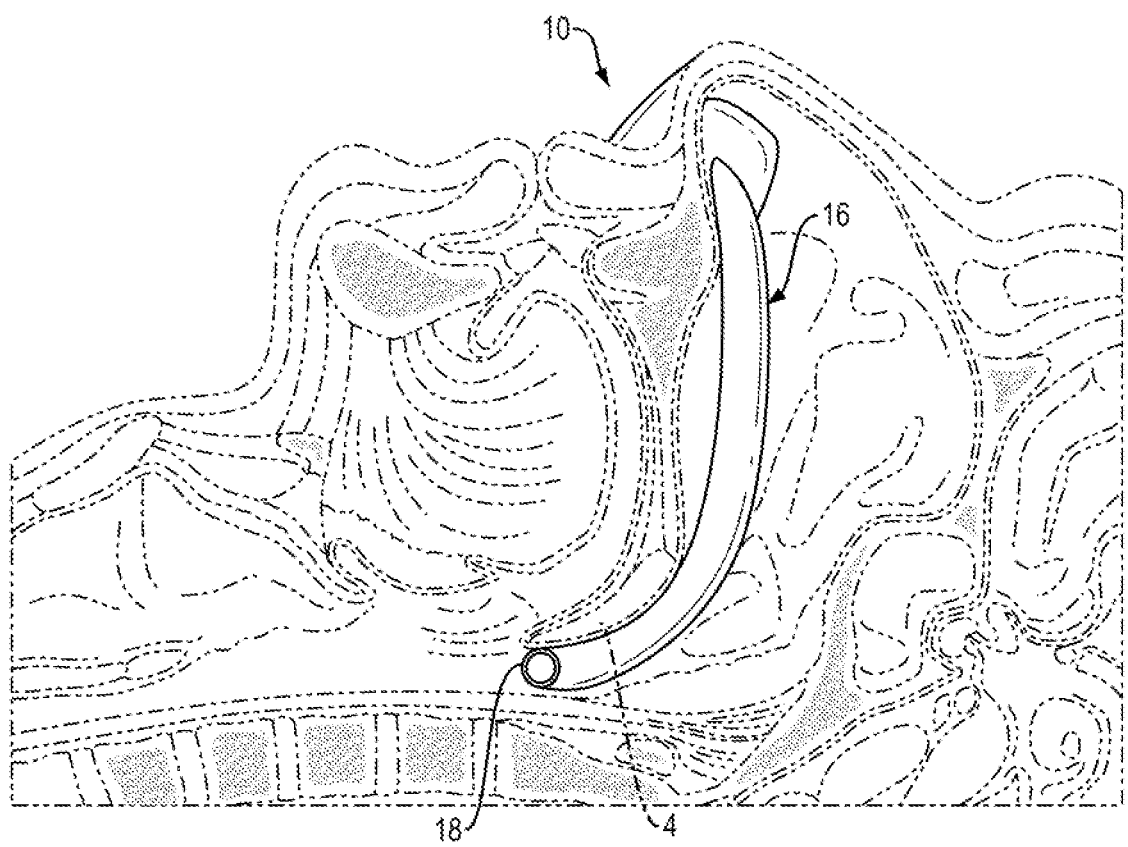

Another drawback of the nasal trumpet is the tube 14 extends past the soft palate. Referring to FIG. 2B, a prior art trumpet 10 inserted into the nose of an anatomical model is shown. More particularly, the tube 16 is of a uniform diameter and extends past the soft palate 4. The distal end of the tube 16 has an opening for air and a conical extension (not shown) that can be inflated. The conical extension is located below the soft palate and is not effective in opening up the nasopharyngeal airway as described herein.

Figure 3A:
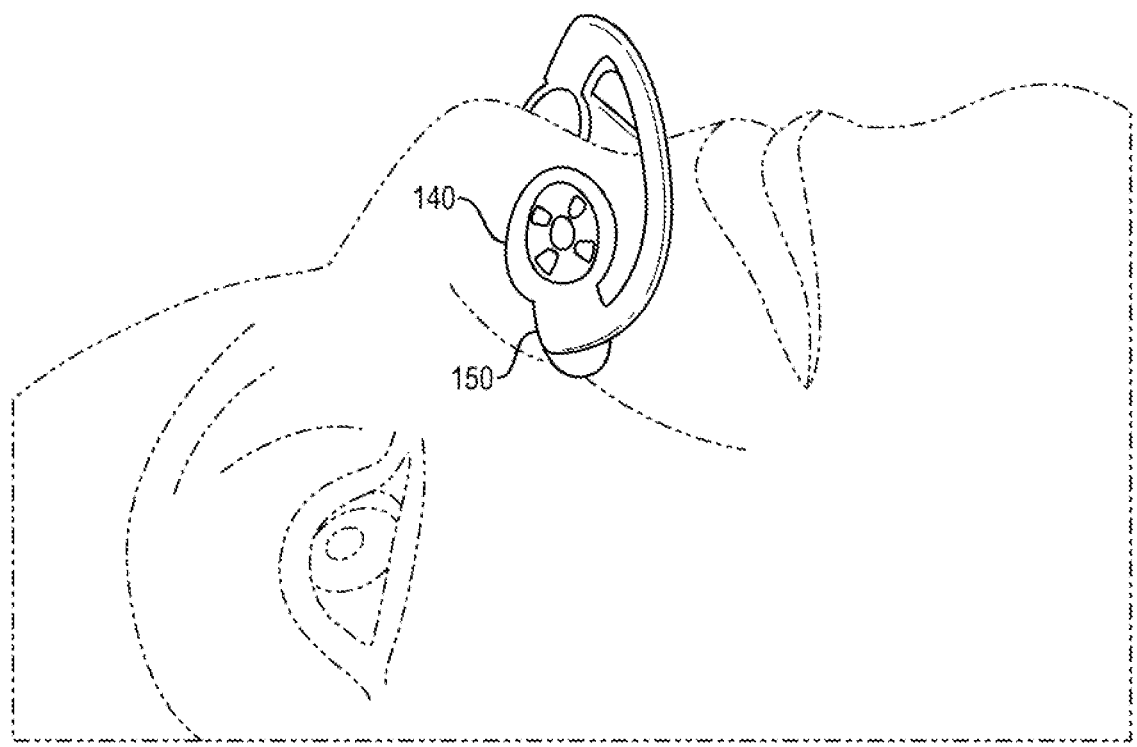
FIG. 3A and FIG. 3B show one embodiment of the nasopharyngeal device of the present invention inserted into an anatomical model.
Figure 3B:
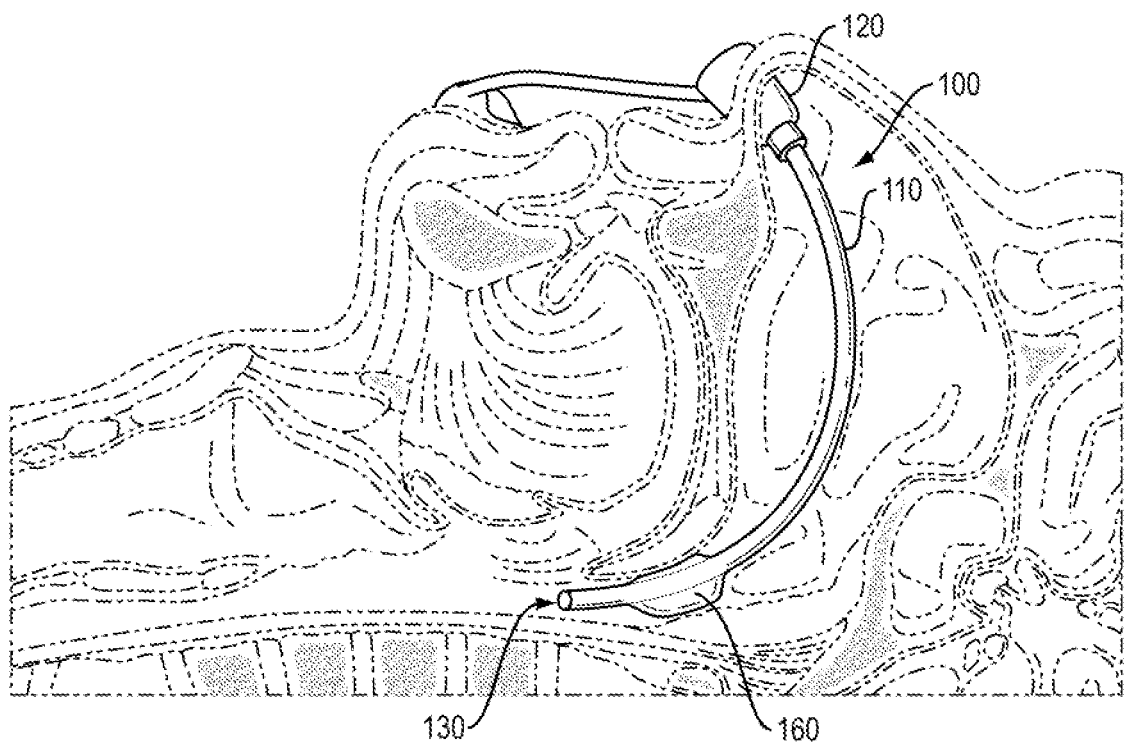

Referring to FIG. 3A and FIG. 3B, embodiments of the nasopharyngeal device of the present invention inserted into the nose of anatomical model are shown. More particularly, one embodiment of the nasopharyngeal device 100 of the present invention comprises a solid-walled, semi-rigid tube 110 with a proximal end 120 and a distal end 130. In certain embodiments, the proximal end has a cup 140 that attaches to the tube and prevents the tube from being inserted too far into the patient. In certain embodiments of the present invention, the cup extends minimally beyond the nostril. It is to he understood that the term cup as used herein also refers to tubular or conical structures or flatter structures commonly called buttons. In certain embodiments, the nasopharyngeal device of the present invention has two cups that attach to each nostril of the patient for improved comfort and stability. In certain embodiments of the present invention, the cup does not extend beyond the nostril of the patient when inserted. In certain embodiments, the cup further comprises a dip 150 for securing the cup to the patient's nostril. In certain embodiments, the device of the present invention comprises a reversibly inflatable balloon-cuff 160 near the distal end of the tube that is inflated and deflated via the tube.

Referring to FIGS. 4A-4F embodiments of the nasopharyngeal device of the present invention are shown. More particularly, one embodiment of the nasopharyngeal device of the present invention comprises a solid-walled, semi-rigid tube 110 with a proximal end 120 and a distal end 130. In certain embodiments, a reversibly inflatable balloon-cuff 160 is located near or at the distal end of the tube such that it aligns with the soft palate for inflation and subsequent opening of the nasopharyngeal airway. It is understood that the placement of the balloon-cuff may vary for patients depending on their anatomy, but that the alignment must coincide with the soft palate for proper functioning. In certain embodiments, the balloon-cuff 160 can be inflated via a port 175 in the tube 110 with the use of a bulb, a syringe 180, or other mechanisms known to those of skill in the art. In certain embodiments, the balloon-cuff is inflated using a syringe with a luer lock fitting.

Figure 4A:
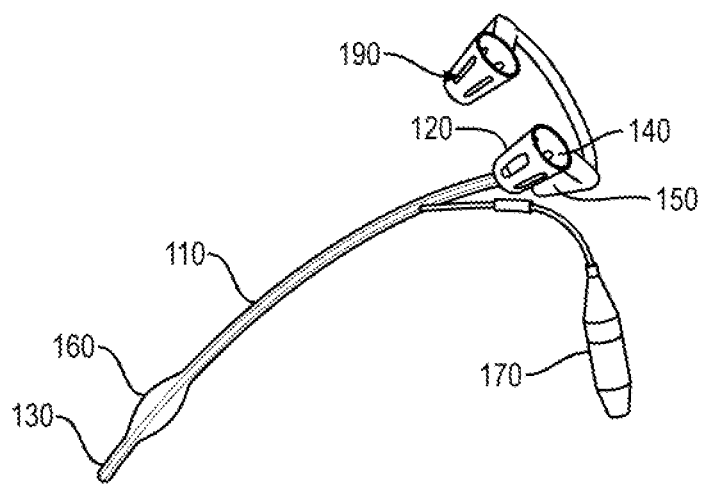
FIGS. 4A-4F show embodiments of the nasopharyngeal device of the present invention.
Figure 4B:
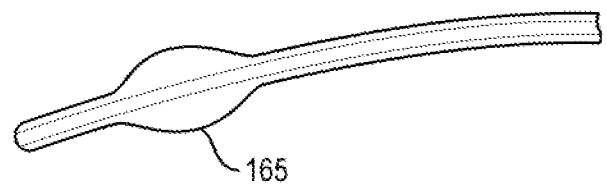
Figure 4C:
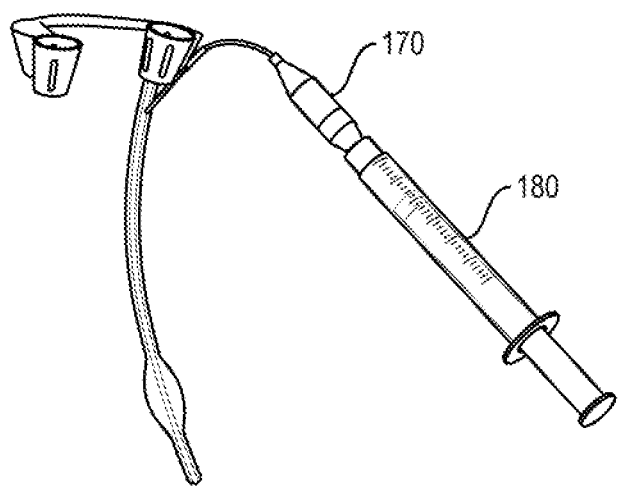
Figure 4D:
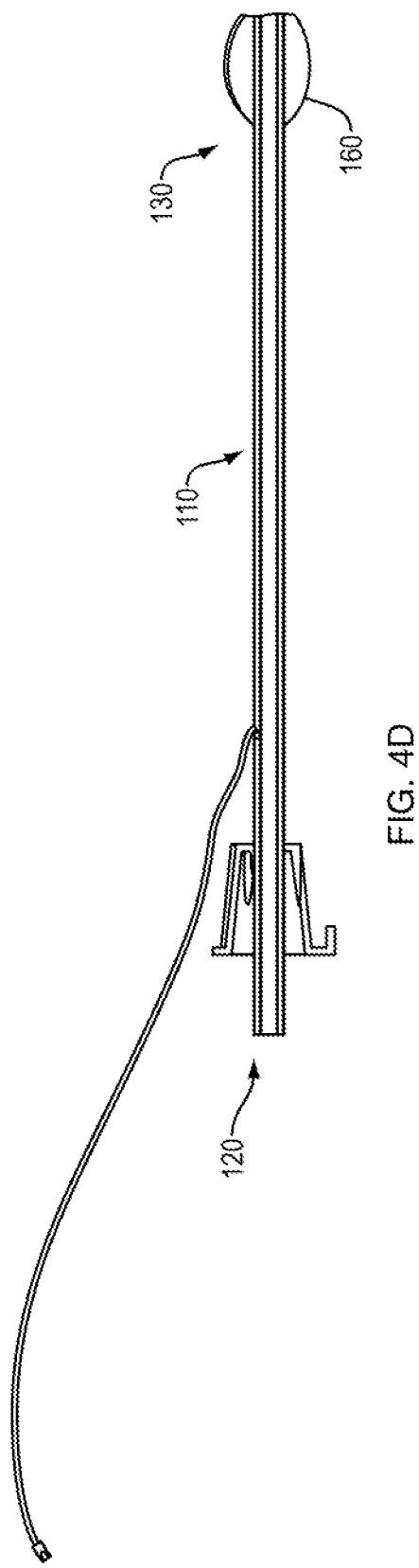
Figure 4E:
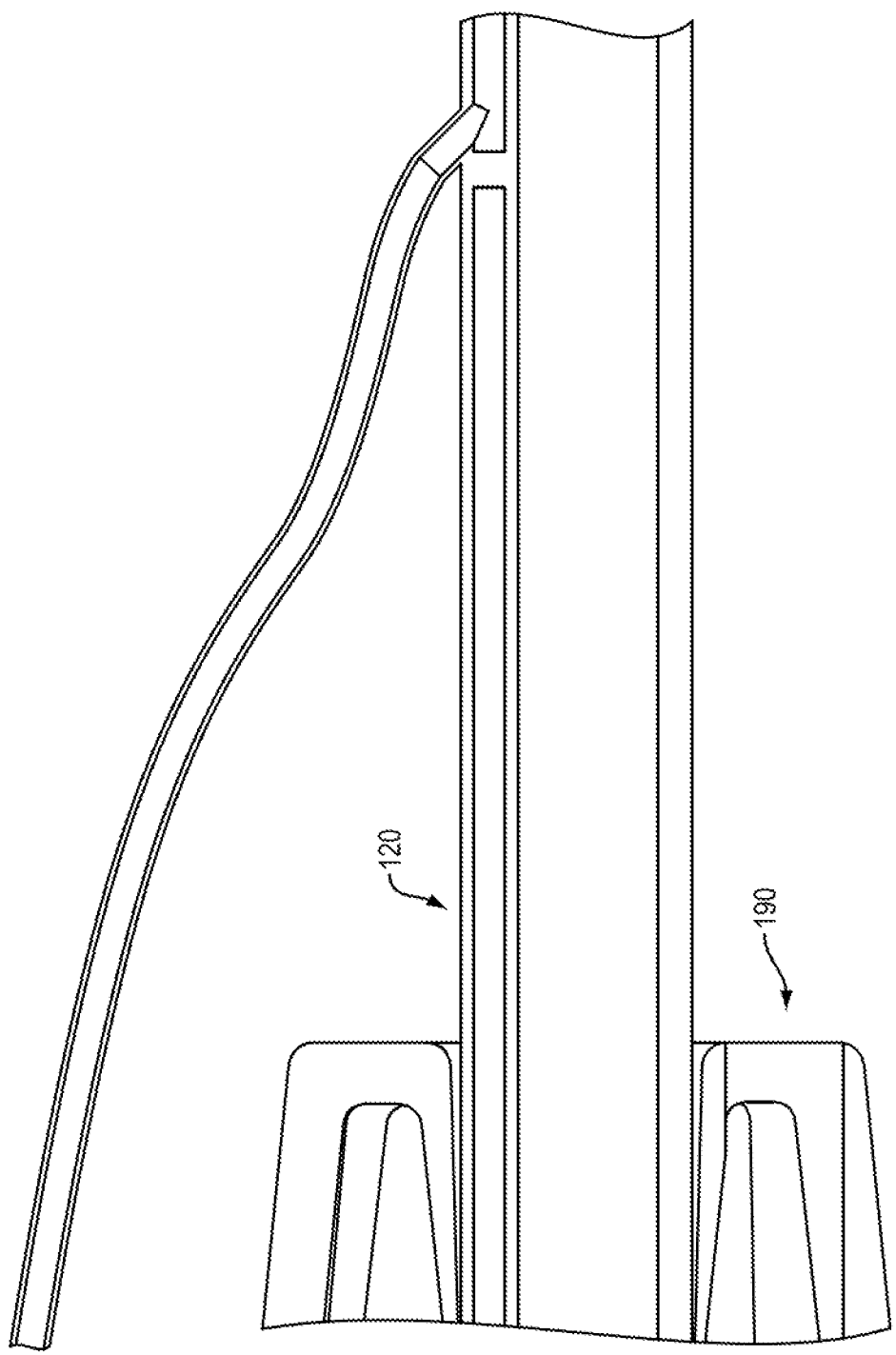
Figure 4F:
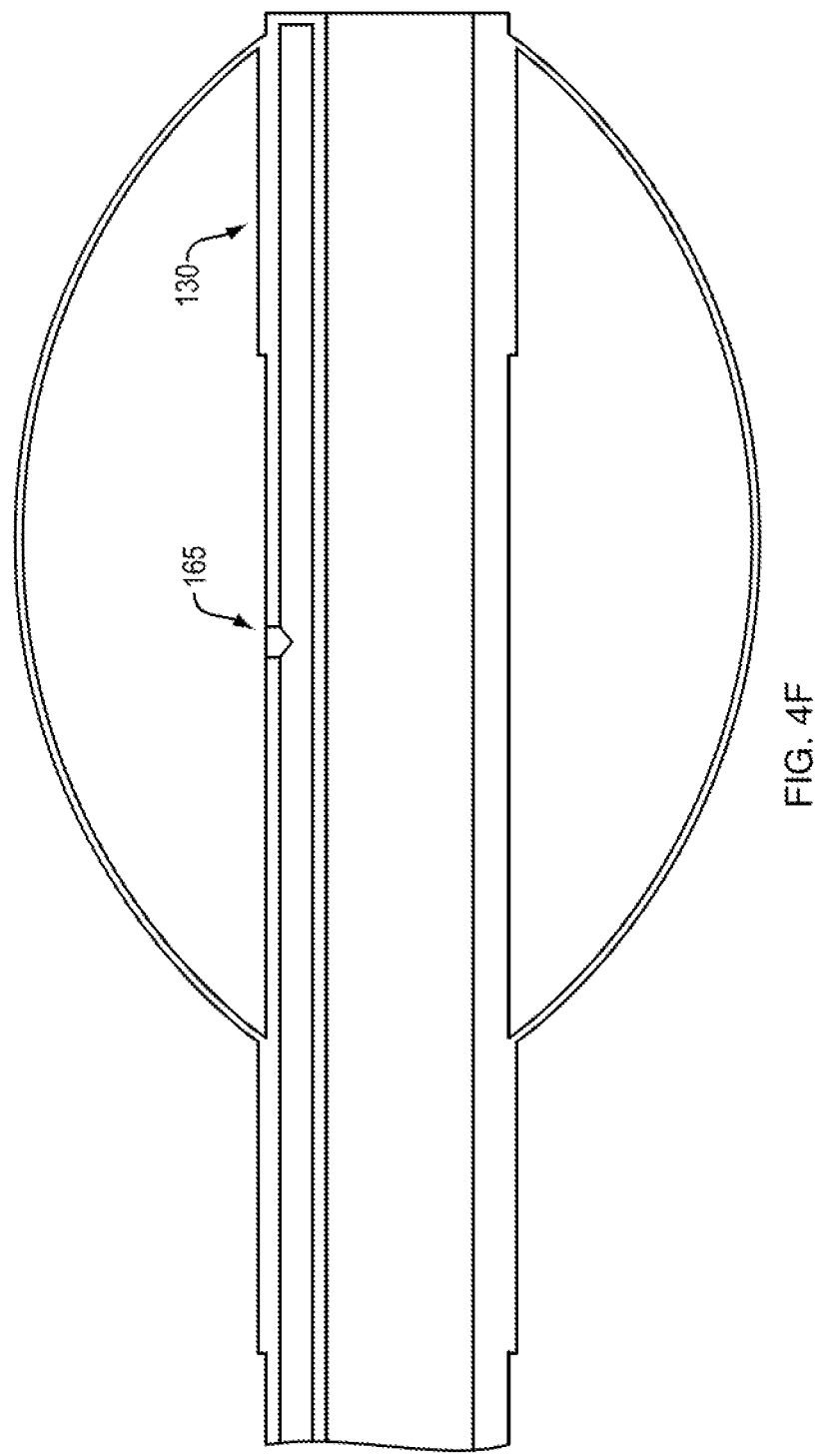
Figure 4G:
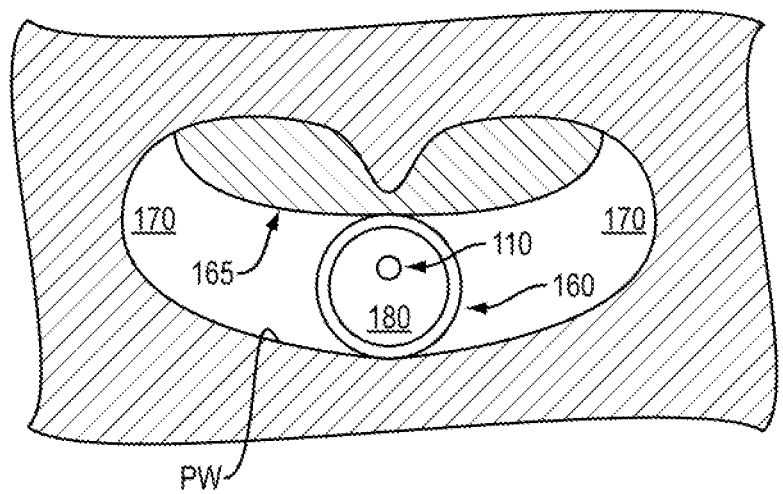
FIG. 4G is a cross-sectional view of an embodiment of the present invention in a user's nasopharyngeal airway.

As shown in FIG. 4G, when inserted into the nasopharyngeal airway and inflated the balloon-cuff 160 stents the soft palate 165 thereby maintaining the patency of the nasopharyngeal airway 170 and allowing airflow through the airway around the tube.

Figure 4H:
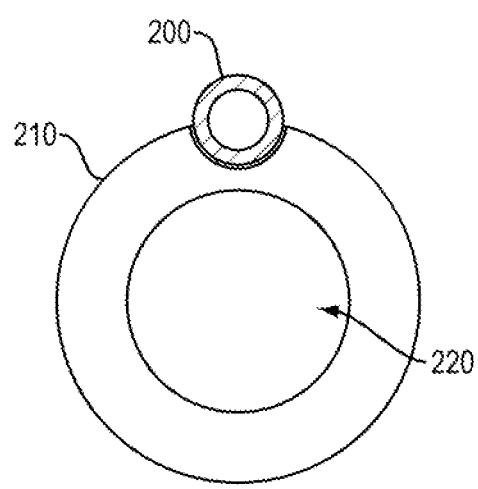
FIG. 4H is a cross-sectional view of a device in the prior art.

It should be noted that, as shown in FIG. 4G, when inflated the balloon-cuff 160 defines an area 180 through which airflow is not allowed except through the tube. This is in contrast to the prior art, as described in U.S. Pat. No. 8,833,373 which discloses a tube 200 with an inflatable balloon-cuff 210 defining an interior through hole 220 extending the length of the balloon-cuff, allowing air flow through the hole, as shown in FIG. 4H. The present invention has the advantage of simpler, and less expensive, construction and a narrower balloon-cuff to insert through a patient's nose.

Still referring to FIGS. 4A-4F, in certain embodiments, the cup comprises a series of perforations, slots, holes, and the like 190 to allow more air to enter a patient's nostril when the device is installed. In prior art nasal trumpets, mechanisms for inflation, if present, are located on the trumpet and/or the trumpet is solid thus reducing the amount of an entering the patient with each breath. By doing so, current devices, by design, have occluded the nasal airway that surrounds the central lumen of the tube. One of the dangers associated with OSA is deceased oxygen intake. The nasopharyngeal device of the present invention helps to reduce or eliminate that risks associated with decreased oxygen intake in a multitude of ways.

According to one embodiment the tube 110 may be formed from a variety of suitable materials known to those skilled in the art, for example, but not limited to, polyvinyl chloride. Likewise, the balloon-cuff 160 may be formed from a variety of suitable materials such as, for example, but not limited to, polyvinyl chloride or polyurethane.

Figure 5A:
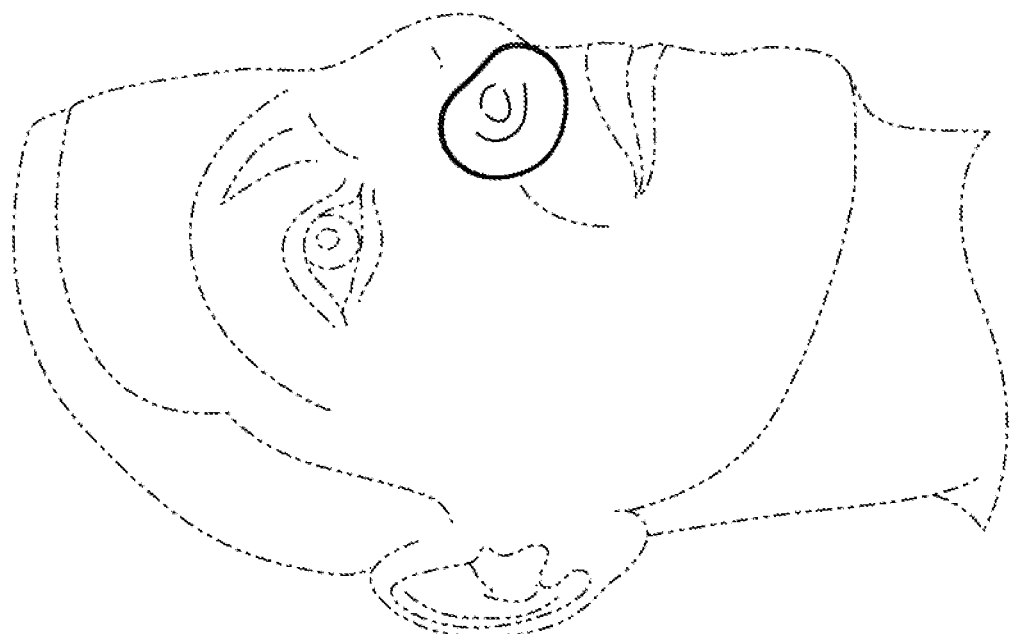
FIG. 5A shows a prior art nasal trumpet inserted into an anatomical model.
Figure 5B:
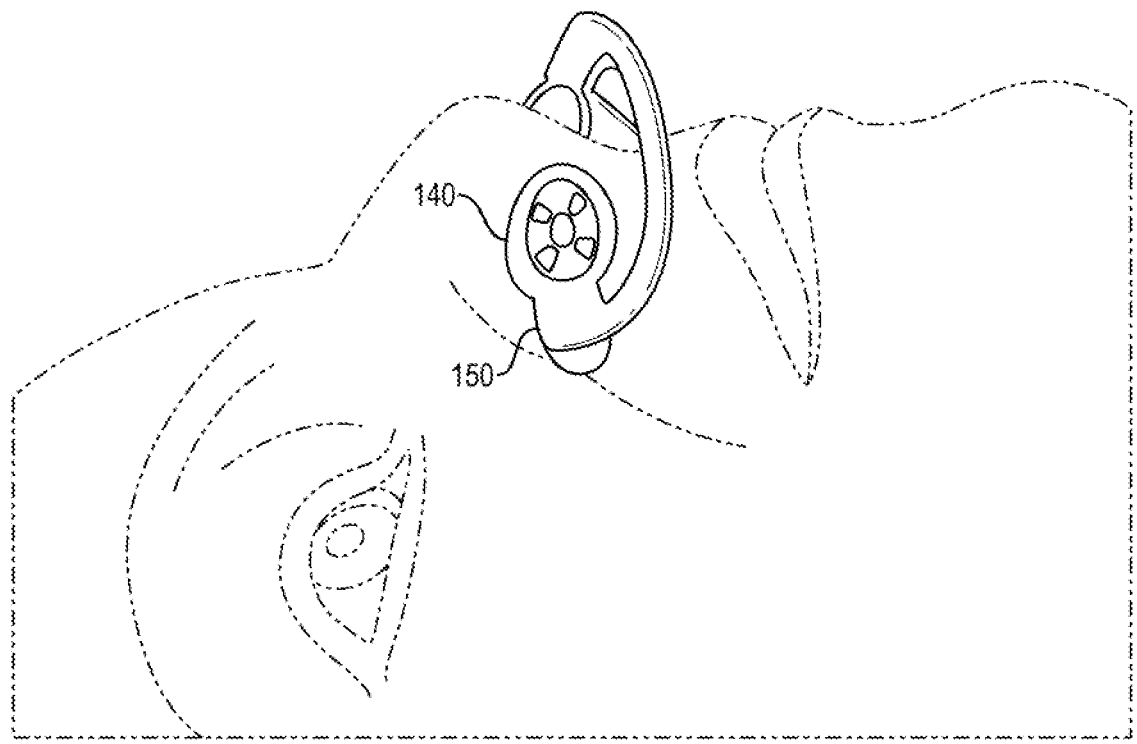
FIG. 5B shows one embodiment of the nasopharyngeal device of the present invention inserted into an anatomical model.

The proximal end of the nasopharyngeal device of the present invention is designed with multiple perforations that enable the user to breathe not only through the lumen of the tube but also around the tube. See, for example, FIG. 5B. This design feature is extremely important since it allows the device to be thinner, thus it is more easily and painlessly passed through the nose. The tube's primary purpose is to carry the inflatable distal balloon-cuff down to the level of the soft palate for its ultimate inflation. The inflated balloon-cuff pushes the soft palate forward which opens up the nasopharyngeal airway, keeping it from collapsing. Moreover, because of the smaller, thinner size of the nasopharyngeal device of the present invention a standard, pliable balloon-cuff found on traditional endotracheal tubes is used in certain embodiments.

Figure 6A:
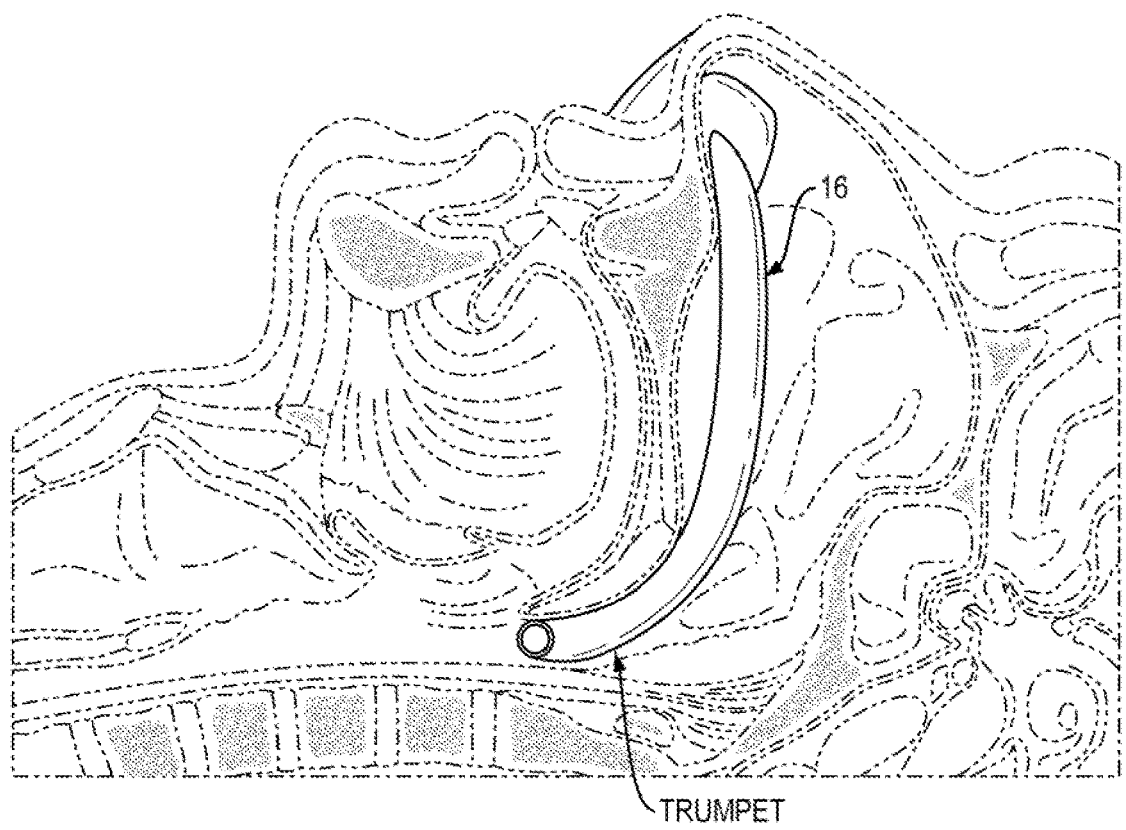
FIG. 6A shows a prior art nasal trumpet inserted into an anatomical model.
Figure 6B:
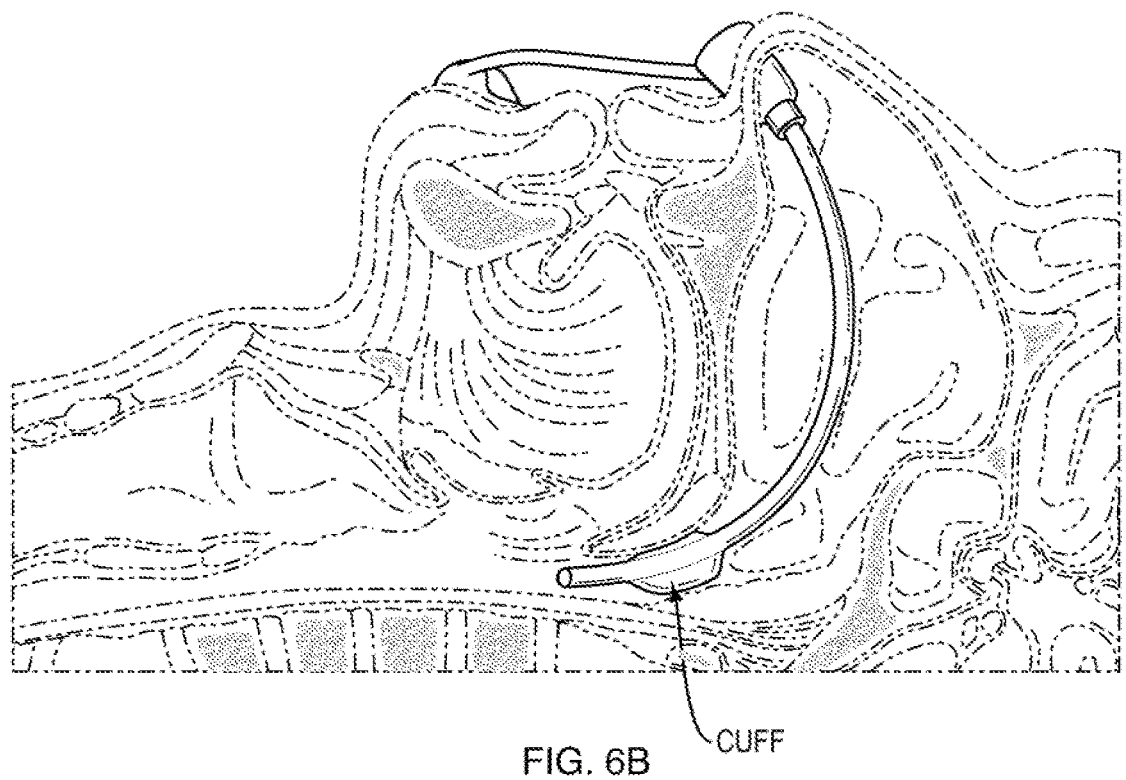
FIG. 6B shows one embodiment of the nasopharyngeal device of the present invention inserted into an anatomical model.

Referring to FIG. 6A, a prior art nasal trumpet inserted into an anatomical model is shown. More particularly, the trumpet is constructed of a thick-walled and wide-diameter tube with a flange at the proximal end to help prevent loss of the tube in the patient. The tube is large and causes patient discomfort when installed, thus leading to a compliance problems. In contrast, Referring to FIG. 6B, one embodiment of the nasopharyngeal device of the present invention inserted into the nose of an anatomical model is shown. More particularly, the nasopharyngeal device comprises a small, semi-rigid, solid-walled tube with a balloon-cuff located at the distal end and adjacent to the soft palate. In certain embodiments, the device comprises a cup with perforations, holes, slots, or the like to allow for increased air intake for the patient.

In certain embodiments, the maximum outer diameter of the tube is fitted to suit the individual patient. In certain embodiments, the outer diameter of the tube is about 2 mm. In certain embodiments, the outer diameter of the tube is about 3 mm. In certain embodiments, the outer diameter of the tube is about 4 mm, although it can be larger.

Figure 7B:
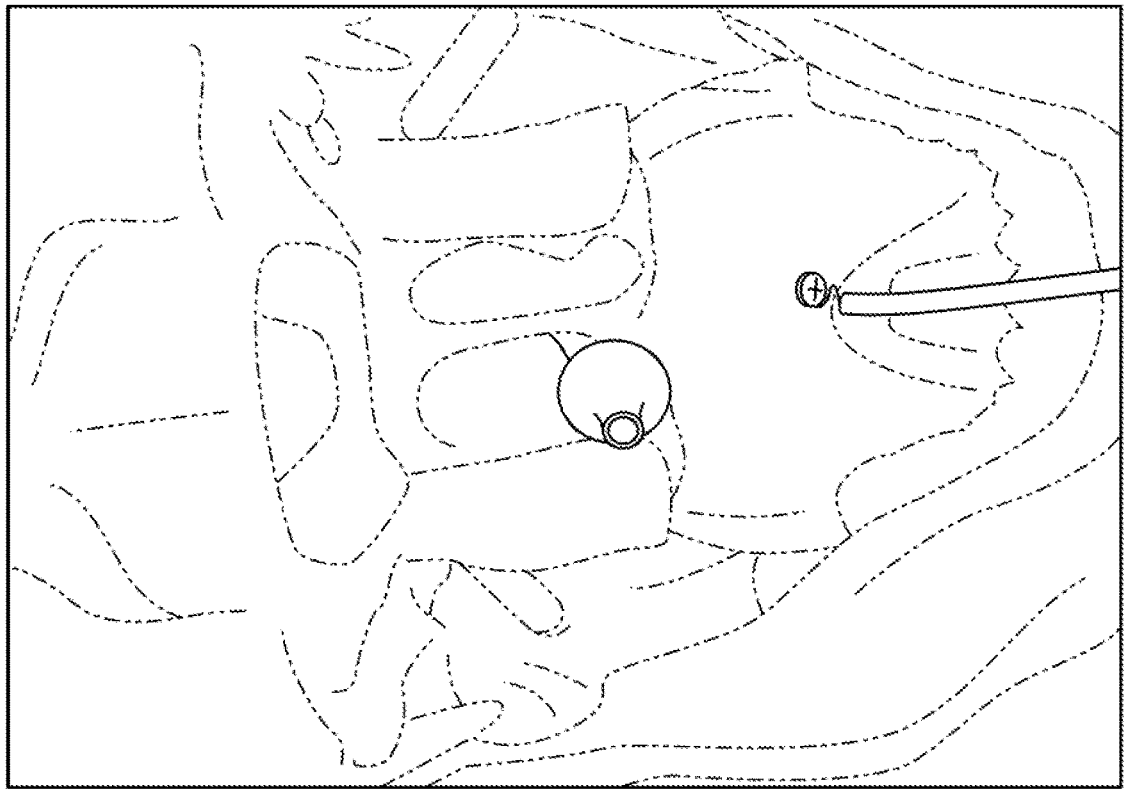
FIG. 7B shows one embodiment of the nasopharyngeal device of the present invention inserted into the nose of an anatomical model with the distal end protruding past the nasal aperture.
Figure 7A:
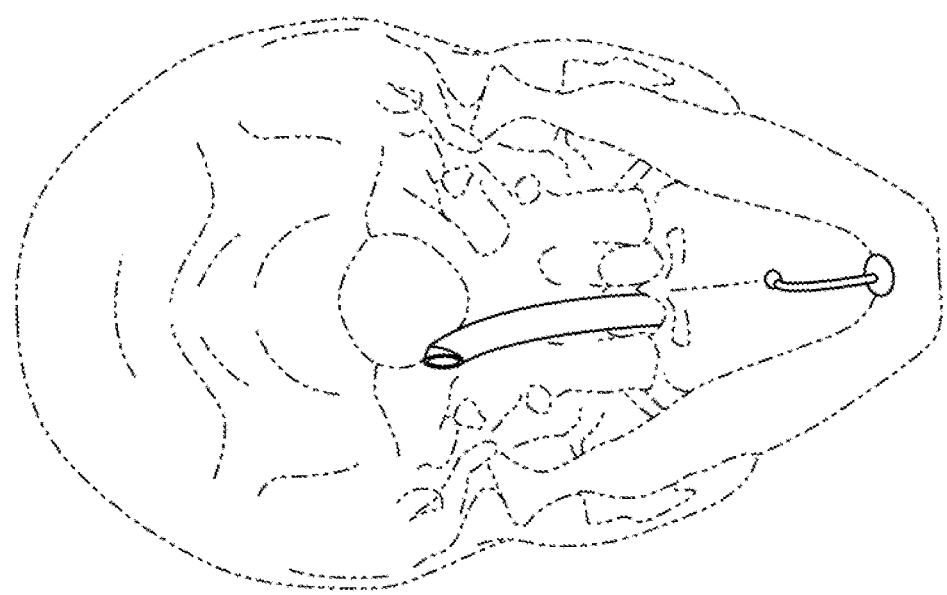
FIG. 7A shows a prior art nasal trumpet inserted into the nose of an anatomical model with the distal end protruding past the nasal aperture.

Referring to FIG. 7A, a prior art nasal trumpet, inserted into the nose of an anatomical model and protruding past the nasal aperture is shown. More particularly, the tube of the prior art nasal trumpet is large and obscures and blocks the passageway thus reducing the amount of air available to the patient.

Figure 8B:
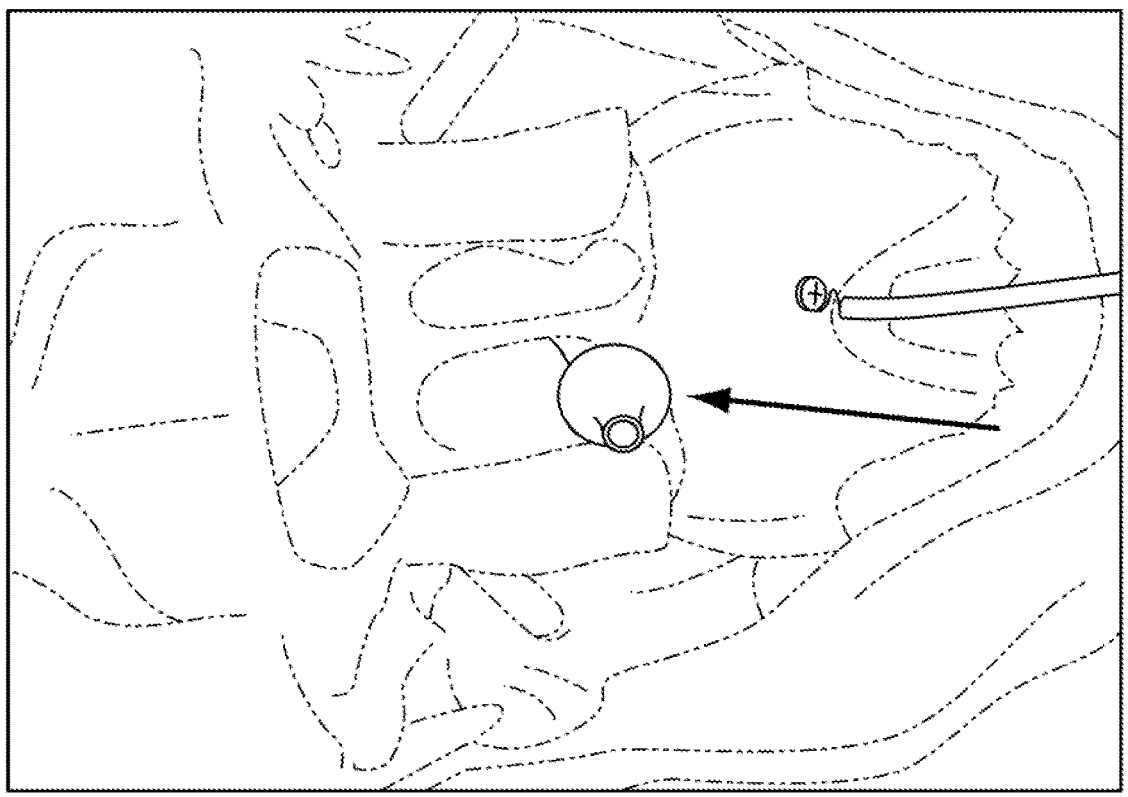
FIG. 8A and FIG. 8B show embodiments of the nasopharyngeal device of the present invention inserted into the nose of an anatomical model with the distal end protruding past the nasal aperture.
Figure 8A:
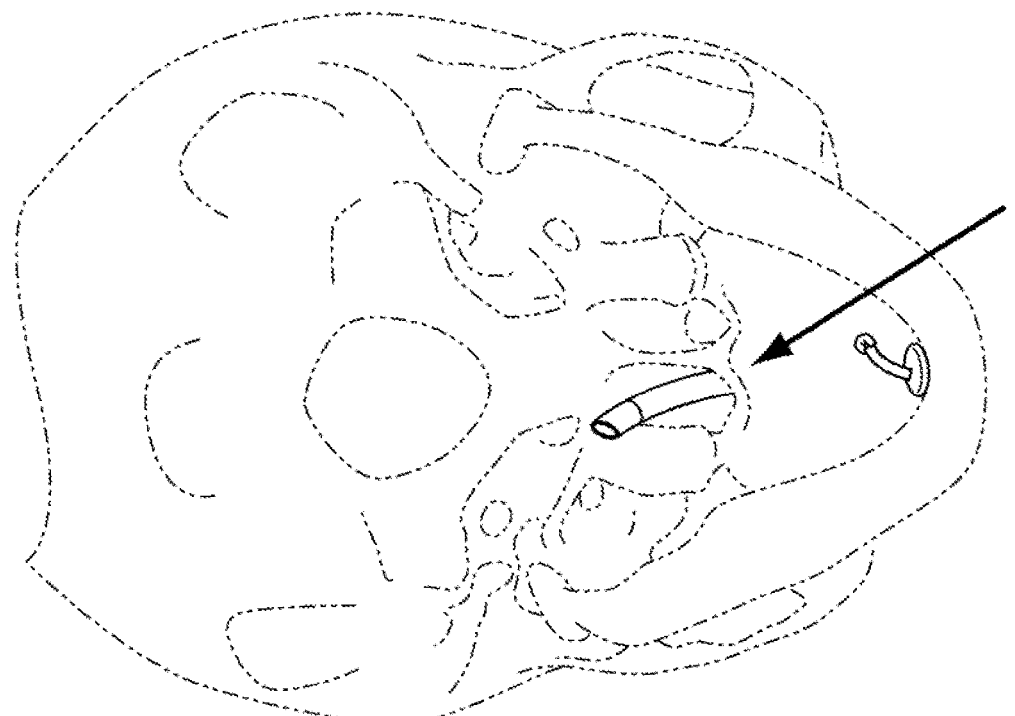

Referring to FIG. 7B, one embodiment of the nasopharyngeal device of the present invention inserted into the nose of an anatomical model and protruding past the nasal aperture is shown. More particularly, the balloon-cuff is located just outside the nasal aperture and aligned with the soft palate, not shown, so as to provide an opening of the airway while not obscuring or blocking the airway. See also, FIG. 8A and FIG. 8B where embodiments of the nasopharyngeal device of the present invention are inserted into the nose of an anatomical model. There, the balloon-cuff protrudes just past the nasal aperture and does not block the airway.

In certain embodiments, the length of the tube is fitted to suit the individual patient. The outer diameter and length of the tube will vary with the patient's nasal anatomy and the size of their head and length of their soft palate. Measurements will he made in order to ensure that the balloon-cuff of the nasopharyngeal device is able to advance the palate appropriately in order to open up the retro palatal space. In certain embodiments, the balloon-cuff is comprised of soft polymers.

Figure 9:
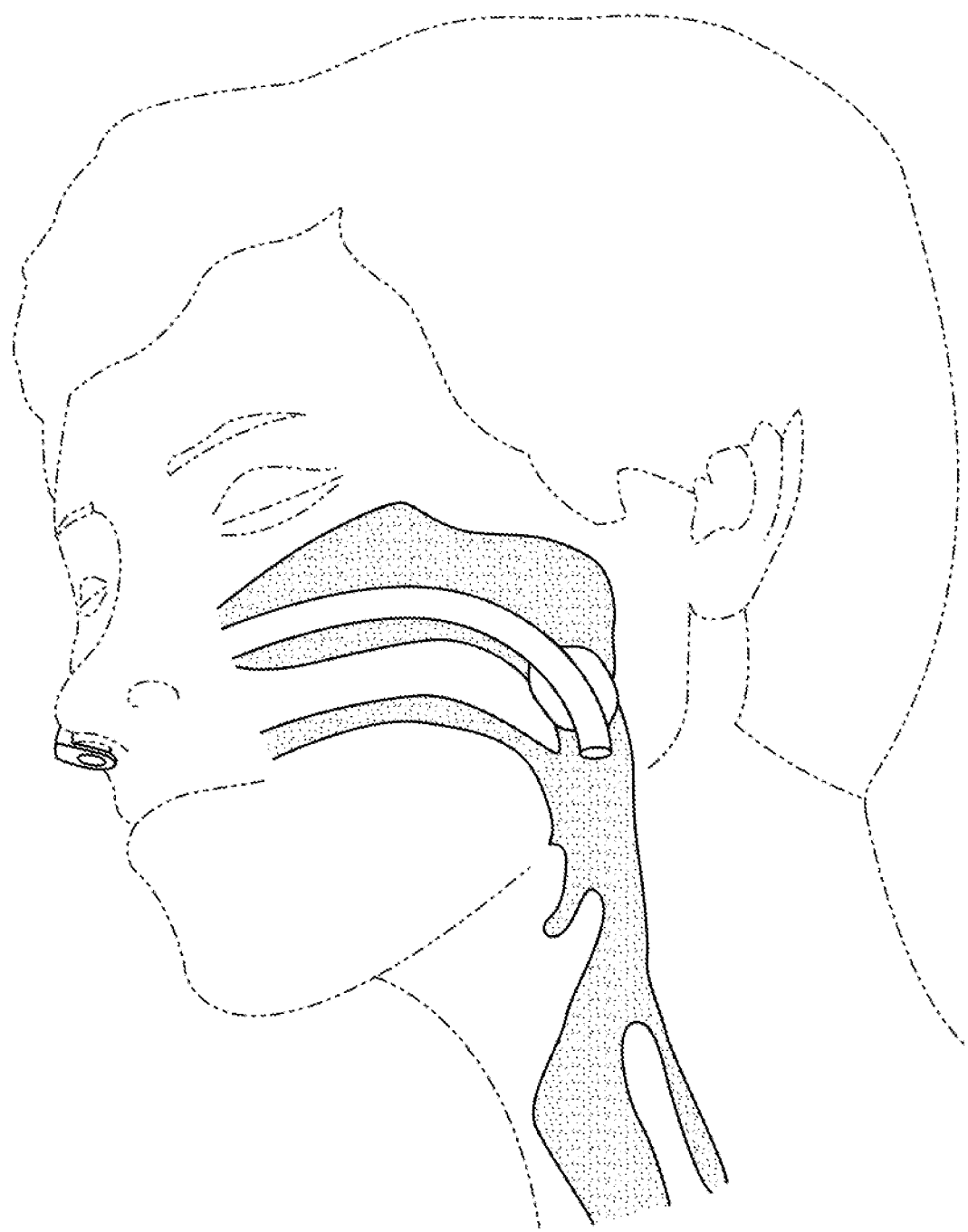
FIG. 9 shows one embodiment of the nasopharyngeal device of the present invention inserted into the nose of an anatomical model.

Referring to FIG. 9, one embodiment of the nasopharyngeal device of the present invention inserted into the nose of a patient is shown. More particularly, in certain embodiments there is a single cup on the proximal end of the device. In certain embodiments, the cup comprises a clip for holding the cup in place on the patient's nostril.

Figure 10:
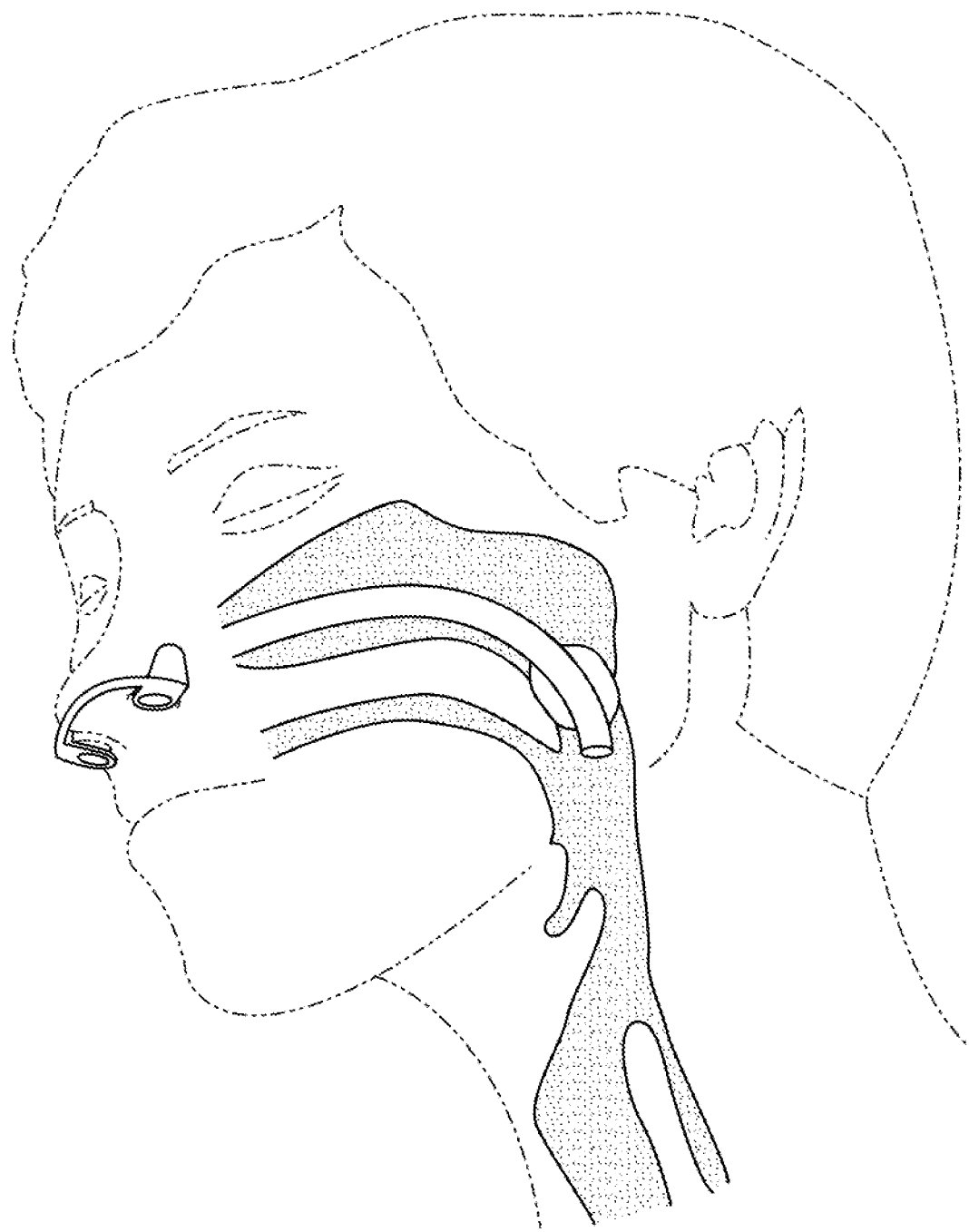
FIG. 10 shows one embodiment of the nasopharyngeal device of the present invention inserted into the nose of an anatomical model.

Referring to FIG. 10, one embodiment of the nasopharyngeal device of the present invention inserted into the nose of a patient is shown. More particularly, in certain embodiments there is a pair of cups on the proximal end of the device. In certain embodiments, the cups comprise a clip for holding the cups in place on the patient's nostrils.

In certain embodiments of the present invention, the device is a modified, shortened, nasopharyngeal airway tube. In certain embodiments, the device has an elongated inflatable balloon-cuff near its distal end, which rests behind the soft palate and posterior nasopharyngeal wall. Upon inflation, the soft palate is moved forward enabling the patient to breathe freely. In certain embodiments, the proximal end of the device is located at the nasal vestibule (nostril) and is tapered, flexible and has an attached soft plastic clamp, which keeps it secured to the nose during sleep.

In certain embodiments, the diameter and length of the tube will vary depending upon the anatomical dimensions of the patient.

While the principles of the invention have been described herein, it is to he understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed:

1. A nasopharyngeal device for obstructive sleep apnea syndrome, comprising a semi-rigid, solid-walled tube, the tube comprising:
  a proximal end;
  a distal end;
  a proximal opening; and
  a distal opening;
a reversibly inflatable balloon-cuff located at the distal end of the tube, wherein:
  a length of the tube is configurable such that when inserted to define a nasopharyngeal airway the balloon-cuff is positioned substantially in the nasopharynx, and
  when inflated, the balloon-cuff maintains patency of the nasopharyngeal airway by advancing forward and stenting open the soft palate and defines an area of the nasopharyngeal airway substantially in the nasopharynx through which air flow is not allowed except through the distal opening of the tube,
at least one cup located at the proximal end of the tube;
an access port located remote from the balloon-cuff;
an inflation port located at the balloon-cuff; and
an inflation channel operably coupling the access port to the inflation port and for inflating and deflating the balloon-cuff via the access port and the inflation port.

2. The nasopharyngeal device of claim 1, wherein the length of the tube is configured to position the balloon-cuff proximal to the soft palate when in use.

3. The nasopharyngeal device of claim 1, wherein there is a pair of cups.

4. The nasopharyngeal device of claim 1, further comprising a clip on the cup to secure the device on a patient's nostril.

5. The nasopharyngeal device of claim 1, wherein the cup further comprises perforations.

6. The nasopharyngeal device of claim 1, wherein the cup further comprises slots.

7. The nasopharyngeal device of claim 1, wherein the cup further comprises holes.

8. A method of reducing obstructive sleep apnea, comprising:
  providing a nasopharyngeal device, comprising:
    a semi-rigid, solid-walled tube, the tube comprising:
      a proximal end;
      a distal end;
      a proximal opening; and
      a distal opening;
    a reversibly inflatable balloon-cuff located at the distal end of the tube;
    at least one cup located at the proximal end of the tube;
    an access port located remote from the balloon-cuff;
    an inflation port located at the balloon-cuff; and
    an inflation channel operably coupling the access port to the inflation port and for inflating and deflating the balloon-cuff via the access port and the inflation port,
  inserting the nasopharyngeal device into the nasopharynx such that the balloon-cuff is positioned substantially in the nasopharynx; and
  inflating the balloon-cuff via the inflation port and the inflation channel thereby defining a nasopharyngeal airway by:
    opening the airway by advancing forward the soft palate; and
    defining an area substantially in the nasopharynx through which air flow is not allowed except through the distal opening of the tube.

9. The method of reducing obstructive sleep apnea of claim 8, wherein the tube has a length such that the balloon-cuff is proximal to the soft palate when in use.

10. The method of reducing obstructive sleep apnea of claim 8, wherein there is a pair of cups.

11. The method of reducing obstructive sleep apnea of claim 8, further comprising a clip on the cup to secure the device on a patient's nostril.

12. The method of reducing obstructive sleep apnea of claim 8, wherein the cup further comprises perforations.

13. The method of reducing obstructive sleep apnea of claim 8, wherein the cup further comprises slots.

14. The method of reducing obstructive sleep apnea of claim 8, wherein the cup further comprises holes.

15. The nasopharyngeal device of claim 1, wherein at least a portion of the channel is located along an outer surface of the tube wall.

16. The nasopharyngeal device of claim 1, wherein at least a portion of the inflation channel is located beneath the balloon-cuff.

17. The nasopharyngeal device of claim 1, wherein an outer diameter of the tube is 2 mm to 4 mm, inclusive.

18. The method of reducing obstructive sleep apnea of claim 8, further comprising operably coupling an inflation Mechanism to an access port and operating the inflation mechanism to induce airflow through the channel and inflate the balloon-cuff.

19. The method of reducing obstructive sleep apnea of claim 8, further comprising operably coupling a deflation mechanism to an access port and operating the deflation mechanism to induce airflow through the channel and deflate the balloon-cuff.

20. A nasopharyngeal device for obstructive sleep apnea syndrome, comprising
  a semi-rigid, solid-walled tube, the tube comprising:
    a proximal end;
    a distal end;
    a proximal opening; and
    a distal opening;
  a reversibly inflatable balloon-cuff located at the distal d of the tube that when inflated maintains patency of a nasopharyngeal airway by advancing forward and stenting open the soft palate and defines an area substantially in the nasopharynx through which air flow is not allowed except through the distal opening of the tube;
  at least one cup located at the proximal end of the tube, wherein the position of the balloon-cuff relative to the at least one cup is adjustable in order to position the balloon cuff substantially in the nasopharynx when the tube is inserted into the nasopharynx;
  an access port located remote from the balloon-cuff;
  an inflation port located at the balloon-cuff; and
  an inflation channel operably coupling the access port to the inflation port and for inflating and deflating the balloon-cuff via the access port and the inflation port.

* * * * *

UNITED STATES PATENT AND TRADEMARK OFFICE
CERTIFICATE OF CORRECTION

PATENT NO. : 10,569,037 B2  
APPLICATION NO. : 14/621722  
DATED : February 25, 2020  
INVENTOR(S) : John M. O'Day Page 1 of 1

It is certified that error appears in the above-identified patent and that said Letters Patent is hereby corrected as shown below:

In the Specification

| | | |
|---|---|---|
| Column 1, | Line 25, | change "pressure ("CPAP"),"  to --pressure ("CPAP").-- |
| Column 2, | Line 32, | change "not Meant to" to --not meant to-- |
| Column 3, | Line 31, | change "area Involved in" to --area involved in-- |
| Column 4, | Line 20, | change "tube 16 has" to --tube 18 has-- |
| Column 4, | Line 34, | change "to he understood" to --to be understood-- |
| Column 4, | Line 42, | change "a dip 150" to --a clip 150-- |
| Column 5, | Line 21, | change "of an entering" to --of air entering-- |
| Column 6, | Line 25, | change "will he made" to --will be made-- |
| Column 6, | Line 57, | change "to he understood" to --to be understood-- |

In the Claims  
Claim 18, Column 8, Line 28, change "Mechanism to an" to --mechanism to an--  
Claim 20, Column 8, Line 43, change "the distal d" to --the distal end--

Signed and Sealed this  
Seventh Day of April, 2020

Andrei Iancu  
*Director of the United States Patent and Trademark Office*